United States Patent
Hillisch et al.

(10) Patent No.: US 6,956,031 B2
(45) Date of Patent: Oct. 18, 2005

(54) 11β-SUBSTITUTED 19-NOR-17-α-PREGNA-1,3,5(10)-TRIEN-17β-OLS WITH A 21,16α-LACTONE RING

(75) Inventors: Alexander Hillisch, Jena (DE); Walter Elger, Berlin (DE); Rolf Bohlmann, Berlin (DE); Jens Hoffmann, Muehlenbeck (DE)

(73) Assignee: Schering Aktiengesellschaft, Berlin (DE)

( * ) Notice: Subject to any disclaimer, the term of this patent is extended or adjusted under 35 U.S.C. 154(b) by 258 days.

(21) Appl. No.: 10/397,855

(22) Filed: Mar. 27, 2003

(65) Prior Publication Data

US 2004/0014735 A1 Jan. 22, 2004

Related U.S. Application Data

(60) Provisional application No. 60/374,517, filed on Apr. 23, 2002.

(30) Foreign Application Priority Data

Mar. 27, 2002 (DE) .......................... 102 14 179

(51) Int. Cl.[7] ........................... A61K 31/58; C07J 71/00
(52) U.S. Cl. ......................................... 514/174; 540/65
(58) Field of Search .............................. 540/65; 514/174

*Primary Examiner*—Barbara P. Badio
(74) *Attorney, Agent, or Firm*—Millen, White, Zelano & Branigan, P.C.

(57) ABSTRACT

This invention relates to new 19-nor-17α-pregna-1,3,5(10)-trien-17β-ols with a 21,16α-lactone ring with a long-chain substituent in 11β-position of general formula II

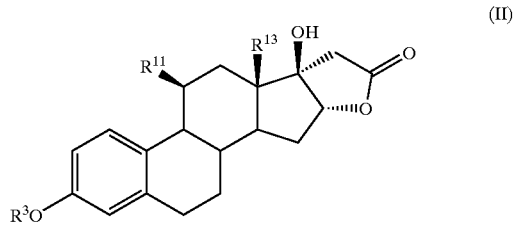

(II)

in which $R^{11}$ is a long-chain alkyl radical that has a nitrogen atom that can be substituted in terminal position with a perfluoroalkyl group. The compounds act in a tissue-selective manner as pure antiestrogens and are suitable for the production of pharmaceutical agents because of these properties.

17 Claims, No Drawings

11β-SUBSTITUTED 19-NOR-17-α-PREGNA-1,3,5(10)-TRIEN-17β-OLS WITH A 21,16α-LACTONE RING

This application claims the benefit of the filing date of U.S. Provisional Application Ser. No. 60/374,517 filed Apr. 23, 2002.

This invention relates to new 11β-long-chain-substituted 19-nor-17α-pregna-1,3,5(10)-trien-17β-ols with a 21,16α-lactone ring, process for their production and pharmaceutical preparations that contain these compounds as well as the use of these compounds for the production of pharmaceutical agents.

Estrogens exert their physiological action on receptor proteins, the estrogen receptors (ERs). In this case, these are nuclear-position transcription factors that can be activated by ligands. Until a few years ago, it was assumed that estrogens exert their action via a single receptor.

Only since 1996 has it become known that two subtypes of the estrogen receptor exist (ERα and ERβ) (Kuiper et al., Proc. Natl. Acad. Sci. USA 93, 1996, 5925–5930). Both are distinguished in their expression pattern in different tissues. Thus, for example, ERβ predominates over ERα in the rat prostates, while ERα predominates in the rat uterus. Areas were identified in the brain in which in each case only one of the two ER subtypes is expressed (Shugrue et al., Steroids 61, 1996, 678–681; Li et al., Neuroendocrinology 66, 1997, 63–67). Both ERα and ERβ are expressed in bones (Kuiper et al., Frontiers in Neuroendocrinology 1998, 19: 253–286), blood vessels (Iafrati et al., Nature Med. 1997, 3: 545–48) and normal breast tissue (Gustafsson and Warner, J. Steroid Biochem. Mol. Biol. 74, 2000, 245–248).

In malignant, degenerated breast tissue, an up-regulation of ERα expression as well as a reduced ERβ expression were observed in several independent works (Leygue et al., Cancer Res. 61, 1998, 3197–3201; Iwao et al., Int. J. Cancer, 88, 2000, 733–736; Lacennec et al., Endocrinology 142, 2001, 4120–4130; Roger et al., Cancer Res. 61, 2001, 2537–2541). ERβ knock-out mice (deficient ERβ) exhibit an abnormal epithelial growth of the breast and an over-expression of proliferation marker Ki67 (Gustafsson and Warner, 2000). Also, an inverse correlation between ERβ expression and Ki67 was detected in humans (Roger et al., 2001). In addition, ERβ acts as an inhibitor of ERα transcriptional activity and lowers the cellular sensitivity to estradiol (Hall and McDonnell, Endocrinology 140, 1999, 5566–5578). These data support the hypothesis that ERβ, i.a., shows a protective factor against the mitogenic activity of estrogens that is mediated by ERα. ERβ can therefore be regarded as an endogenic antagonist of ERα.

In patents by Katzenellenbogen et al. (WO 00/19994) and Loozen et al. (WO 00/31112), subtype-specific estrogen receptor ligands, i.a., ERα-selective compounds, are described.

WO 01/00652 disclosed 11β-long-chain-substituted estratrienes of general formula I,

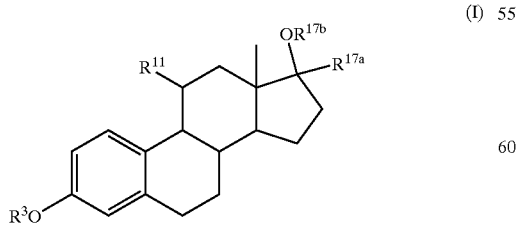

(I)

in which R11 is a long-chain radical that has a nitrogen atom as well as optionally a sulfur atom, which in addition can be functionalized in terminal position with a perfluoroalkyl group or an optionally substituted aryl radical. The compounds have at their disposal antiestrogenic or tissue-selective estrogenic properties and are suitable for the production of pharmaceutical agents.

In the un-prepublished application DE 100 48 634, 19-nor-17α-pregna-1,3,5(10)-trien-17β-ols with a 21,16α-lactone ring are described as selective estrogens, which show preference for estrogen receptor α in contrast to standard estrogens such as estradiol.

The object of this invention consists in making available new compounds that have in vitro a dissociation with respect to their binding to estrogen receptor preparations of rat prostates and rat uteri and in vivo an antiproliferative action via the preferential antagonizing of ERα, without preventing the positive properties of the ERβ. This also includes a preferential suppression of the expression of ERα without reduction of the ERβ expression.

The object is [achieved] according to this invention by the preparation of novel 19-nor-17α-pregna-1,3,5(10)-trien-17β-ols with a 21,16α-lactone ring with a long-chain substituent in 11β-position of general formula II

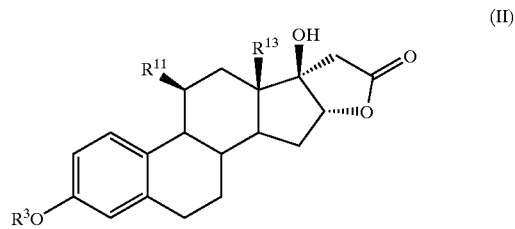

(II)

in which
R³ represents a hydrogen atom, a C₁₋₄-alkyl, C₂₋₆-acyl or tri(C₁₋₄-alkyl)silyl group or a group R¹⁸SO₂—,
whereby
R¹⁸ represents a group R¹⁹R²⁰N—,
in which
R¹⁹ and R²⁰, independently of one another, are a hydrogen atom, a C₁₋₅-alkyl radical, a group C(O)R²¹ and
in which
R²¹ represents a straight-chain or branched hydrocarbon radical with up to 12 carbon atoms, which in addition can contain up to three double bonds, a C₃₋₇-cycloalkyl radical, an aryl radical, which optionally can be substituted, an aralkyl radical or an alkylaryl radical,
and
R¹¹ represents a radical of formula —B-Z-R²²,
whereby
B stands for a straight-chain or branched-chain alkylene with 4 to 9 carbon atoms, and
Z stands for —NR²³ and R²³ stands for a C₁–C₃-alkyl group, and
R²² stands for a hydrogen atom, a straight-chain or branched-chain alkyl, alkenyl or alkinyl group with 3 to 11 carbon atoms or for a grouping -D-CₙF₂ₙ₊₁, whereby D is a straight-chain or branched-chain alkylene, alkenylene or alkinylene group with 3 to 11 carbon atoms, and n is an integer from 1 to 5,
and
R¹³ stands for a methyl or ethyl group.

Another subject of this invention relates to pharmaceutical agents that contain a compound of general formula II or their pharmaceutically acceptable addition salts with organic or inorganic acids.

Unless defined in more detail otherwise in terms of this invention, this is an aryl radical that optionally can be substituted by a phenyl, 1- or 2-naphthyl radical, whereby the phenyl radical is preferred. Unless expressly indicated otherwise, aryl always also includes a heteroaryl radical. Examples of a heteroaryl radical are the 2-, 3- or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2-, 4- or 5-pyrimidinyl radical or the 3- or 4-pyridazinyl radical.

As substituents for an aryl, heteroaryl or aralkyl radical, for example, a methyl, ethyl, trifluoromethyl, pentafluoroethyl, trifluoromethylthio, methoxy, ethoxy, nitro, cyano, halogen (fluorine, chlorine, bromine, iodine), hydroxy, amino, mono ($C_{1-8}$-alkyl) or di($C_{1-8}$-alkyl)amino, whereby both alkyl groups are identical or different, and di(aralkylamino), whereby both aralkyl groups are identical or different, can be mentioned.

As representatives of alkyl radicals or straight-chain or branched-chain alkyl groups with up to 12 carbon atoms in terms of $R^3$, $R^{19}$ and $R^{20}$ or $R^{21}$, for example, methyl, ethyl, propyl, isopropyl, butyl, isobutyl, tert-butyl, pentyl, isopentyl, neopentyl, hexyl, heptyl, and decyl can be mentioned. Methyl, ethyl, propyl and isopropyl are preferred.

Alkylene, alkenylene or alkinylene radicals in the range of 3 to 11 carbon atoms in terms of B or R22 are defined as, for example, propylene, butylene, isobutylene, pentylene, methyl-butylene, hexylene, heptylene, octylene or butenylene, 2-butenylene, 3-butenylene, 1-ethyl-ethenylene, 2-ethylethenylene, 1-methyl(1-propenylene), 1-methyl(2-propenylene), 2,3-dimethyl-1-butenylene, 2,3-dimethyl-2-butenylene, 3-dimethyl-1-butenylene, 2-methyl-2-butenylene, hexenylene, 4-methyl-1-pentenylene, heptenylene, 1-octenylene, trans-2-octenylene or 1-butinylene, 2-butinylene, 3-butinylene, 3-methyl(1-butinylene), 1-methyl(3-butinylene), 1-pentinylene, 2-pentinylene, 2-hexinylene, 3-hexinylene, heptinylene, 1-octinylene, or 4-octinylene.

The alkyl groups can be partially or completely substituted by 1–5 halogen atoms, for example fluorine atoms.

As perfluorinated alkyl groups, for example, trifluoromethyl and pentafluoroethyl can be mentioned. Representatives of the partially fluorinated alkyl groups are, for example, 2,2,2-trifluoroethyl, 5,5,5,4,4-pentafluoropentyl, etc.

$C_{2-6}$-acyl radicals mean, for example, acetyl, propionyl, butyryl, valeroyl, isovaleroyl, pivaloyl, and hexanoyl.

Representatives of the above-mentioned $C_{3-7}$-cycloalkyl group can be, for example, cyclopropyl, cyclobutyl, cyclopentyl, or cyclohexyl.

The hydroxyl group at C-atom 3 can be esterified with an aliphatic, straight-chain or branched-chain, saturated or unsaturated $C_{2-6}$-carboxylic acid. As such carboxylic acids for esterification, the following are considered, for example: acetic acid, propionic acid, butyric acid, isobutyric acid, valeric acid, isovaleric acid or pivalic acid.

As examples of a tri($C_{1-4}$-alkyl) group, a trimethylsilyl group and a tert-butyldimethyl group can be mentioned.

According to the invention, compounds of general formula II

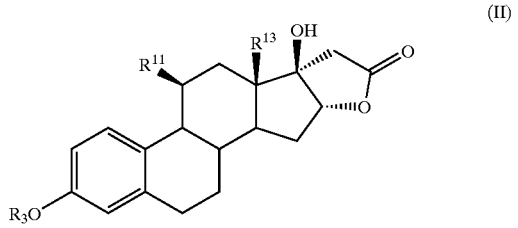

(II)

are preferred, in which $R^3$ means a hydrogen atom or a methyl group and $R^{13}$ means a methyl group, and $R^{11}$ can be selected from the group of the following side chains —$(CH_2)_5N(CH_3)(CH_2)_3C_2F_5$
—$(CH_2)_5N(CH_3)(CH_2)_6C_2F_5$
—$(CH_2)_5N(CH_3)(CH_2)_7C_2F_5$
—$(CH_2)_5N(CH_3)(CH_2)_8C_2F_5$
—$(CH_2)_6N(CH_3)(CH_2)_6C_2F_5$
—$(CH_2)_6N(CH_3)(CH_2)_7C_2F_5$
—$(CH_2)_6N(CH_3)(CH_2)_8C_2F_5$
—$(CH_2)_5N(CH_3)(CH_2)_2C_3F_7$
—$(CH_2)_5N(CH_3)(CH_2)_6C_3F_7$
—$(CH_2)_5N(CH_3)(CH_2)_2C_4F_9$
—$(CH_2)_5N(CH_3)(CH_2)_6C_4F_9$
—$(CH_2)_5N(CH_3)(CH_2)_2C_5F_{11}$
—$(CH_2)_5N(CH_3)(CH_2)_6C_5F_{11}$
—$(CH_2)_5N(CH_3)H$
—$(CH_2)_5N(CH_3)(CH_2)_3H$
—$(CH_2)_5N(CH_3)(CH_2)_6H$
—$(CH_2)_5N(CH_3)(CH_2)_7H$
—$(CH_2)_5N(CH_3)(CH_2)_9H$
—$(CH_2)_5N(CH_3)CH_2CH=CH—C_2F_5$ Especially preferred 11β-long-chain-substituted 19-nor-17α-pregna-1,3,5(10)-trienes with a 21,16α-lactone ring are, for example:

3,17α-Dihydroxy-11β-{5-[methyl-(4,4,5,5,5-pentafluoro-pentyl)-amino]-pentyl}-19-nor-17α-pregna-1,3,5(10)-triene-21,16α-lactone 3,17α-dihydroxy-11β-{5-[methyl-(7,7,8,8,8-pentafluoro-octyl)-amino]-pentyl}-19-nor-17α-pregna-1,3,5(10)-triene-21,16α-lactone 3,17α-dihydroxy-11β-{5-[methyl-(8,8,9,9,9-pentafluoro-nonyl)-amino]-pentyl}-19-nor-17α-pregna-1,3,5(10)-triene-21,16α-lactone 3,17α-dihydroxy-11β-{5-[methyl-(9,9,10,10,10-pentafluoro-decyl)-amino]-pentyl}-19-nor-17α-pregna-1,3,5(10)-triene-21,16α-lactone 3,17α-dihydroxy-11β-{6-[methyl-(7,7,8,8,8-pentafluoro-octyl)-amino]-hexyl}-19-nor-19-nor-17α-pregna-1,3,5(10)-triene-21,16α-lactone 3,17α-dihydroxy-11β-{6-[methyl-(8,8,9,9,9-pentafluoro-nonyl)-amino]-hexyl}-19-nor-17α-pregna-1,3,5(10)-triene-21,16α-lactone 3,17α-dihydroxy-11β-{6-[methyl-(9,9,10,10,10-pentafluoro-decyl)-amino]-hexyl}-19-nor-17α-pregna-1,3,5(10)-triene-21,16α-lactone 3,17α-dihydroxy-11β-{5-[methyl-(3,3,4,4,5,5,5-heptafluoro-pentyl)-amino]-pentyl}-19-nor-17α-pregna-1,3,5(10)-triene-21,16α-lactone 3,17α-dihydroxy-11β-{5-[methyl-(7,7,8,8,9,9,9-heptafluoro-nonyl)-amino]-pentyl}-19-nor-17α-pregna-1,3,5(10)-triene-21,16α-lactone 3,17α-dihydroxy-11β-{5-[methyl-(3,3,4,4,5,5,6,6,6-nonafluoro-hexyl)-amino]-pentyl}-19-nor-17α-pregna-1,3,5(10)-triene-21,16α-lactone 3,17α-dihydroxy-11β-{5-[methyl-(7,7,8,8,9,9,10,10,10-nonafluoro-decyl)-amino]-pentyl}-19-nor-17α-pregna-1,3,5(10)-triene-21,16α-lactone 3,17α-dihydroxy-11β-{5-[methyl-(3,3,4,4,5,5,6,6,7,7,7-undecafluoro-heptyl)-amino]-pentyl}-19-nor-17α-pregna-1,3,5(10)-triene-21,16α-lactone 3,17α-dihydroxy-11β-{5-[methyl-(7,7,8,8,9,9,10,10,11,11,11-undecafluoro-undecyl)-amino]-pentyl}-19-nor-17α-pregna-1,3,5(10)-triene-21,16α-lactone 3,17α-dihydroxy-11β-{5-[methyl-amino]-pentyl}-19-nor-17α-pregna-1,3,5(10)-trien-21,16α-lactone 3,17α-dihydroxy-11β-{5-[methyl-propyl-amino]-pentyl}-19-nor-17α-pregna-1,3,5(10)-triene-21,16α-lactone 3,17α-dihydroxy-11β-{5-[methyl-hexyl-amino]-pentyl}-19-nor-17α-pregna-1,3,5(10)-triene-21,16α-lactone 3,17α-dihydroxy-11β-{5-[methyl-heptyl-amino]-pentyl}-19-nor-17α-pregna-1,3,5(10)-triene-21,16α-lactone 3,17α-dihydroxy-11β-{5-[methyl-nonyl-amino]-pentyl}-19-nor-17α-pregna-1,3,5(10)-triene-21,16α-lactone For the formation of pharmaceutically compatible salts of the compounds of general formula II according to the invention, i.a., hydrochloric acid, hydrobromic acid, sulfuric acid and phosphoric acid are suitable as inorganic acids, and, i.a., acetic acid, propionic acid, maleic acid, fumaric acid, succinic acid, benzoic acid, ascorbic acid, oxalic acid, salicylic acid, tartaric acid, citric acid, lactic acid, malic acid, mandelic acid, cinnamic acid and methanesulfonic acid are suitable as organic acids.

The substances of general formula II according to the invention represent compounds that are distinguished by a new structural element, a 21,16α-lactone ring, compared to the compounds with long-chain 11β-side chains that are known from the prior art. It was found that 11β-substituted 19-nor-17α-pregna-1,3,5(10)-trien-17β-ols with a 21,16α-lactone according to the invention selectively show, in a surprising way, an antagonistic action on the ERα. With the substances according to the invention, it is possible preferably to antagonize the ERα without preventing the positive properties of the ERβ. This also includes a preferential suppression of the expression of ERα without reduction of the ERβ expression.

Biological Characterization of the Compounds According to the Invention

The substances of general formula II according to the invention were tested in various models. Via the selective inhibition of the ERα, the substances according to the invention exert an antiproliferative action in other hormone-modulated tumors in addition to the breast tissue.

Pharmaceutical Preparations and Indications

The compounds of general formula II represent compounds with antiestrogenic action after peroral or parenteral administration.

Moreover, the compounds according to the invention are pure antiestrogens.

This invention comprises the novel substances as pharmaceutical active ingredients, their production, their therapeutic application and the pharmaceutical dispensing forms that contain the new substances. The chemical compounds are new steroidal ERα-selective antagonists.

The new selective ERα antagonists that are described in this patent can be used as individual components or in combination in particular with estrogens or antigestagens in pharmaceutical preparations. The novel selective ERα antagonists are suitable both for treating estrogen-dependent diseases, such as, for example, endometriosis, breast cancer, endometrial carcinoma, antiovulatory infertility and for treating prostate cancer, prostate hyperplasias, melanomas as well as lung cancer.

The compounds of general formula II can be used as components in the products that are described in EP 346014 B1 that contain an estrogen and a pure antiestrogen, namely for simultaneous, sequential or separate use for the selective estrogen therapy of perimenopausal or postmenopausal women.

The compounds of general formula II can be used together with antigestagens (competitive progesterone antagonists) for treating hormone-dependent tumors (EP 310 542 A).

Other indications in which the compounds of general formula II can be used are male hair loss, a diffuse alopecia, an alopecia that is caused by chemotherapy as well as hirsutism (H.-S. Oh, R. C. Smart, Proc. Natl. Acad. Sci. USA, 93, 1996, 12525–12530).

The compounds of general formula II can also be used for the production of pharmaceutical compositions for male and female birth control.

The compounds of general formula II according to the invention and their acid addition salts are suitable for the production of pharmaceutical compositions and preparations. The pharmaceutical compositions or pharmaceutical agents contain as active ingredient at least one or more of the compounds of general formula II according to the invention or their acid addition salts, optionally in combination with other pharmacologically active substances or pharmaceutical adjuvants. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmann's Enzyklopädie der technischen Chemie [Ullmann's Encyclopedia of Technical Chemistry], 4, 1953, 1–39; J. Pharm. Sciences, 52, 1963, 918 ff; issued by Czetsch-Lindenwald, Hilfsstoffe für Pharmazie und angrenzende Gebiete [Adjuvants for Pharmaceutics and Related Fields]; Pharm. Ind. 2, 1961, 72 ff; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G, Aulendorf in Württemberg 1971.

The compounds of general formula II according to the invention can be administered orally or parenterally, e.g., intraperitoneally, intramuscularly, subcutaneously and percutaneously. The compounds can also be implanted in the tissue.

Dosage

The amount of the compounds to be administered fluctuates within a wide range and can cover any effective amount. Based on the condition to be treated and the type of administration, the amount of the administered compound can be 0.1–25 mg/kg of body weight, preferably 0.5–5 mg/kg of body weight. In humans, this corresponds to a daily dose of 5 to 1250 mg. The preferred daily dosage in humans is 50 to 200 mg.

For oral administrations, tablets, film tablets, coated tablets, capsules, pills, powder, solutions or suspensions or else depot forms are suitable. Suitable tablets can be obtained, for example, by mixing active ingredient with known adjuvants, for example inert diluents such as dextrose, sugar, sorbitol, mannitol, polyvinyl pyrrolidone, explosives such as corn starch or alginic acid, binders such as starch or gelatin, lubricants such as magnesium stearate or talc and/or agents for achieving a depot effect such as carboxyl polymethylene, carboxylmethyl cellulose, cellulose acetate phthalate or polyvinyl acetate. The tablets can also consist of several layers.

Correspondingly, coated tablets can be produced by coating cores that are produced analogously to the tablets with agents that are commonly used in tablet coatings, for example polyvinyl pyrrolidone or shellac, gum arabic, talc, titanium oxide or sugar. In this case, the coated tablet shell can also consist of several layers, whereby the adjuvants that are mentioned above in the tablets can be used.

Solutions or suspensions with the compounds of general formula II according to the invention can in addition contain taste-improving agents such as saccharine, cyclamate or sugar as well as, e.g., flavoring substances such as vanilla or orange extract. In addition, they can contain suspension adjuvants such as sodium carboxymethyl cellulose or preservatives such as p-hydroxybenzoates.

The compounds of general formula II that contain capsules can be produced, for example, by the compound of general formula U being mixed with an inert vehicle such as lactose or sorbitol and encapsulated in gelatin capsules.

To achieve a better bioavailability of the active ingredient, the compounds of general formula II can also be formulated as cyclodextrin clathrates. To this end, the compounds are reacted with α-, β- or γ-cyclodextrin or derivatives of the latter (PCT/EP 95/02656).

For parenteral administration, the active ingredients can be dissolved or suspended in a physiologically compatible diluent. As diluents, very often oils with or without the addition of a solubilizer, a surfactant, a suspending agent or emulsifying agent are used. Examples of oils that are used are olive oil, peanut oil, cottonseed oil, soybean oil, castor oil and sesame oil.

The compounds of general formula II can also be formulated in the form of a solution that is intended for oral administration and that in addition to the active compound of general formula II contains a pharmaceutically compatible oil and/or a pharmaceutically compatible lipophilic surfactant and/or a pharmaceutically compatible hydrophilic surfactant and/or a pharmaceutically compatible water-miscible solvent.

To this end, reference is made in addition to WO 97/21440.

The compounds can also be used in the form of a depot injection or an implant preparation that can be formulated in such a way that a delayed release of the active ingredient is made possible.

Implants can be obtained as inert materials, for example biodegradable polymers, or synthetic silicones such as, for example, rubber gum. In addition, the active ingredient can be added, for example, to a patch for percutaneous administration.

For the production of intravaginal systems (e.g., vaginal rings) or intrauterine systems (e.g., pessaries, coils) that are loaded with active compounds of general formula II, various polymers, such as, for example, silicone polymers, ethylene vinyl acetate, polyethylene or polypropylene are suitable.

The compounds of general formula II according to the invention can be produced as described below.

The production of 11β-substituted 19-nor-17α-pregna-1,3,5(10)-trien-17β-ols with a 21,16α-lactone ring can be carried out in a one-stage process from the corresponding 17-oxo compounds or the 17α-cyanomethylated estra-1,3,5 (10)-triene derivatives (non-prepublished DE 100 48 634). The formation of the iminoether and thus also the lactone is connected to the presence of a 17α-cyanomethyl substituent.

Starting substances for the synthesis of the 11β-alkyl-substituted 17β-hydroxy-19-nor-17α-pregna-1,3,5(10)-triene-21,16α-lactone are compounds of general formula III

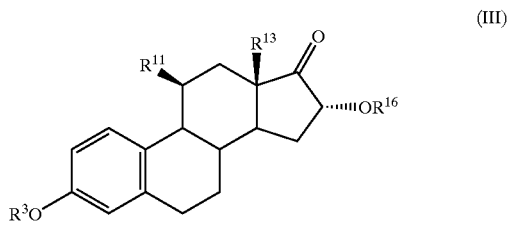

(III)

in which $R^3$ means a $C_{1-4}$-alkyl, $C_{2-6}$-acyl or tri($C_{1-4}$-alkyl)silyl group $R^{11}$ means a radical of formula —B—Y—$R^{24}$, whereby B stands for a straight-chain or branched-chain alkylene group with 4 to 9 carbon atoms, Y stands for an oxygen atom, and $R^{24}$ means a $C_{2-6}$-acyl group or tri($C_{1-4}$-alkyl)silyl group, $R^{13}$ means a methyl or ethyl group, $R^{16}$ means an acetyl or trimethylsilyl group.

The introduction of the 11β-side chain is performed according to methods that are known in the literature. The starting material is an 11β-haloalkyl-estra-1,3,5(10)-trien-3-ol-17-one that is produced analogously to WO01/00652 and according to literature that is cited therein and that is converted in the usual way into a 16α-bromine compound under the protection of the terminal hydroxy function that is contained in 11β as well as the 3-hydroxyl group. Compounds of general formula II are obtained by hydrolysis and protection of the 16α-hydroxy function that is obtained.

As an alternative to this, the introduction of the 16-hydroxy function can be performed by reaction of 17-silyl or 17-acyl enol ethers with peracids and subsequent hydrolysis.

By reaction of the compounds of general formula III with lithium acetonitrile that is produced in situ, a 17α-cyanomethyl-16α-hydroxylate is produced as an intermediate product. By the addition of the 16α-alcoholate to the nitrile group and subsequent hydrolysis of the iminoether that is formed, the lactone is formed.

By the use of compounds according to general formula III, in which $R^{16}$ means trimethylsilyl or acetyl, a portion of about 60% of 17α-cyanomethylated product can be reacted in situ in a one-pot process to form 21,16α-lactone.

After the amine function is introduced into the 11β-hydroxyalkylated side chain, the secondary amine function is alkylated, and the compounds of general formula II according to the invention are obtained.

The saponification of ester groupings as well as etherification and/or esterification of free hydroxyl groups is carried out in each case according to established processes of organic chemistry.

The sulfamates according to the invention are accessible in a way that is known in the art from the corresponding hydroxy steroids by esterification with sulfamoyl chlorides in the presence of a base (Z. Chem. 15, 270–272 (1975); Steroids 61, 710–717 (1996)).

Subsequent acylation of the sulfamide group results in the (N-acyl)sulfamates according to the invention (cf. DE 195 40 233 A1).

The acid addition salts of the compounds of general formula II can also be produced according to standard processes from the free acids of the compounds of general formula II.

The following examples are used for a more detailed explanation of the invention, without being limited thereto:

General Production Process 8 ml (20 mmol) of n-butyllithium solution (2.5 M in toluene) is cooled to −25° C. to −35° C. while being stirred in a reaction vessel that was rendered inert. Then, the solution is diluted by adding 8 ml of tetrahydrofuran while being cooled and reacted with 1.15 ml (22 mmol) of acetonitrile in the above-mentioned temperature range. A white to yellowish suspension of lithium acetonitrile is produced.

A solution of 2.5 mmol of the steroid (e.g., 1.14 g of 11β-hexyl-17-oxo-estra-1,3,5(10)-triene-3,16α-diyl-diacetate) in 8 ml of tetrahydrofuran is added to this suspension while the reaction temperature is kept from −25° C. to −35° C.

After one hour of reaction time in the above-mentioned temperature range, the batch is mixed with water, neutralized with dilute hydrochloric acid, the tetrahydrofuran is distilled off, and the crude product mixture is isolated by extraction with ethyl acetate.

By chromatography on silica gel, the product can be separated and isolated.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

3,17-Dihydroxy-11-{5-[methyl-(6,6,7,7,8,8,8-heptafluoro-octyl)-amino]-pentyl}-19-nor-17-pregna-1,3,5(10)-triene-21,16-lactone a) 11-(5-Chloropentyl)-3,3-(2,2-dimethyltrimethylenedioxy)-5a-hydroxy-estr-9-en-17-one A solution of 34.5 g of 3,3-(2,2-dimethyltrimethylenedioxy)-5a-epoxy-estr-9(11)-en-17-one [Rohde, Ralph; Neef, Guenter; Sauer, Gerhard; Wiechert, Rudolf: *Tetrahedron Lett*. 26; 17; 1985; 2069–2072] in 276 ml of tetrahydrofuran is mixed at room temperature with 4.864 g of copper(1) chloride, stirred for 1 hour, cooled to 3° C. and slowly mixed at this temperature with 1.25 l of a solution—prepared by the reaction of a suspension of 13.48 g of magnesium chips in 132 ml of tetrahydrofuran with 73.28 ml of 1-bromo-5-chloropentane in 1.11 l of tetrahydrofuran. For working-up, 250 ml of a saturated ammonium chloride solution is added in drops, diluted with ethyl acetate, washed with water and common salt solution, dried on sodium sulfate and concentrated by evaporation in a vacuum. 129 g of crude 11-(5-chloropentyl)-3,3-(2,2-dimethyltrimethylenedioxy)-5a-hydroxy-estr-9-en-17-one is obtained.

b) 11-(5-Chloropentyl)-estra-4,9-diene-3,17-dione

A solution of 129 g of crude 11-(5-chloropentyl)-3,3-(2,2-dimethyltrimethylenedioxy)-5a-hydroxy-estr-9-en-17-one in 350 ml of glacial acetic acid is mixed with 175 ml of water and stirred for 24 hours at room temperature. Then, it is evaporated to the dry state in a vacuum, diluted with 1.5 l of ethyl acetate, washed with sodium hydroxide solution, water as well as common salt solution, dried on sodium sulfate and evaporated to the dry state in a vacuum. 58 g of crude 11-(5-chloropentyl)-estra-4,9-diene-3,17-dione is obtained, and after chromatography on silica gel with hexane/acetone, 26 g of pure 11-(5-chloropentyl)-estra-4,9-diene-3,17-dione is obtained.

c) 11-(5-Chloropentyl)-3-hydroxy-estra-1,3,5(10)-trien-17-one

A solution of 6 g of 11-(5-chloropentyl)-estra-4,9-diene-3,17-dione in 100 ml of ethanol is mixed at room temperature with 1 g of palladium on carbon and refluxed under a hydrogen atmosphere for 0.5 hour. Then, the catalyst is filtered off, it is evaporated to the dry state in a vacuum and chromatographed on silica gel with hexane/acetone. 6.2 g of 11-(5-chloropentyl)-3-hydroxy-estra-1,3,5(10)-trien-17-one is obtained.

d) 11-(5-Chloropentyl)-3,17-diacetoxy-estra-1,3,5(10),16-tetraene

A solution of 6 g of 11-(5-chloropentyl)-3-hydroxy-estra-1,3,5(10)-trien-17-one in 136 ml of isopropenyl acetate is mixed with 1.9 g of para-toluenesulfonic acid, and it is refluxed for 24 hours. Then, it is diluted with ethyl acetate, washed with sodium bicarbonate as well as common salt solution, dried on sodium sulfate, evaporated to the dry state in a vacuum and chromatographed on silica gel with hexane/acetone. 6.2 g of 11-(5-chloropentyl)-3,17-diacetoxy-estra-1,3,5(10),16-tetraene is obtained.

e) 3-Acetoxy-16-bromo-11-(5-chloropentyl)-estra-1,3,5(10)-trien-17-one

A solution of 6.2 g of 11-(5-chloropentyl)-3,17-diacetoxy-estra-1,3,5(10),16-tetraene in 95 ml of dimethylformamide is mixed at 0° C. first with 9.05 ml of sodium acetate solution (10%) and then with 2.6 g of N-bromosuccinimide, and it is stirred for one hour. Then, it is mixed with water, extracted with ethyl acetate, washed with sodium sulfate solution as well as common salt solution, dried on sodium sulfate and evaporated to the dry state in a vacuum. 15.3 g of crude 3-acetoxy-16-bromo-11-(5-chloropentyl)-estra-1,3,5(10)-trien-17-one is obtained.

f) 11-(5-Chloropentyl)-3,16-dihydroxy-estra-1,3,5(10)-trien-17-one

A solution of 15.3 g of crude 3-acetoxy-16-bromo-11-(5-chloropentyl)-estra-1,3,5(10)-trien-17-one in 237 ml of pyridine is mixed with 79 ml of water and then with 50 ml of sodium hydroxide solution (1N) and stirred for 24 hours at room temperature. Then, 25 ml of hydrochloric acid (2N) is added, it is evaporated to the dry state in a vacuum, diluted with 1 l of ethyl acetate, washed with hydrochloric acid (2N), washed neutral with water, washed with common salt solution, dried on sodium sulfate and evaporated to the dry state in a vacuum. 4.2 g of crude 11-(5-chloropentyl)-3,16-dihydroxy-estra-1,3,5(10)-trien-17-one is obtained, and after chromatography on silica gel with hexane/ethyl acetate, 2.5 g of pure 11-(5-chloropentyl)-3,16-dihydroxy-estra-1,3,5(10)-trien-17-one is obtained.

g) 3,16-Diacetoxy-11-(5-chloropentyl)-estra-1,3,5(10)-trien-17-one

A solution of 2.4 g of 11-(5-chloropentyl)-3,16-dihydroxy-estra-1,3,5(10)-trien-17-one in 30 ml of pyridine is mixed with 15 ml of acetic anhydride and stirred for 24 hours at room temperature. Then, 150 ml of hydrochloric acid (2N) is added, extracted with 300 ml of ethyl acetate, washed with hydrochloric acid (2N), washed with water, sodium bicarbonate solution as well as common salt solution, dried on sodium sulfate and evaporated to the dry state in a vacuum. 3.1 g of crude 3,16-diacetoxy-11-(5-chloropentyl)-estra-1,3,5(10)-trien-17-one is obtained, and after chromatography on silica gel with hexane/acetone, 2.6 g of pure 3,16-diacetoxy-11-(5-chloropentyl)-estra-1,3,5(10)-trien-17-one is obtained.

h) 11-(5-Chloropentyl)-3,17-dihydroxy-19-nor-17-pregna-1,3,5(10)-trien-21,16-lactone 14.2 ml of tetrahydrofuran as well as 2.05 ml of acetonitrile are added to 14.2 ml of a butyllithium solution (2.5 molar in toluene) at −25° C., and it is stirred for 10 minutes. Then, a solution of 2.1 g of 3,16-diacetoxy-11-(5-chloropentyl)-estra-1,3,5(10)-trien-17-one in 14.1 ml of tetrahydrofuran is added in drops, and it is stirred for another hour at −35 to −25° C. For working-up, it is mixed with water, weakly acidified with 2N hydrochloric acid, diluted with ethyl acetate, washed with water as well as common salt solution, dried on sodium sulfate, and evaporated to the dry state in a vacuum. 3.3 g of crude 11-(5-chloropentyl)-3,17-dihydroxy-19-nor-17-pregna-1,3,5(10)-trien-21,16-lactone is obtained, and after chromatography on silica gel with dichloromethane/acetone, 0.8 g of pure 11-(5- chloropentyl)-3,17-dihydroxy-19-nor-17-pregna-1,3,5(10)-trien-21,16-lactone is obtained as crystals with a melting point of 181.7° C.

[a]D=+53.8° in chloroform i) 3,17-Dihydroxy-11-{5-[methyl-(6,6,7,7,8,8,8-heptafluoro-ocatyl)-amino]pentyl}-19-nor-17-pregna-1,3,5 (10)-triene-21,16-lactone A solution of 100 mg of 11-(5-chloropentyl)-3,17-dihydroxy-19-nor-17-pregna-1,3,5(10)-trien-21,16-lactone in 2 ml of dimethylformamide is stirred with 93 mg of 6,6,7,7,8,8,8-heptafluoro-octyl-methylamine, 109 mg of sodium iodide and 48 mg of sodium bicarbonate for 24 hours at a bath temperature of 80° C. Then, it is diluted with ethyl acetate, washed with water as well as common salt solution, dried on sodium sulfate and evaporated to the dry state in a vacuum. 0.13 g of crude product is obtained. A solution of 130 mg of this crude product in 5 ml of acetone is mixed with 7 drops of perchloric acid (70%) and stirred for 1 hour at room temperature. Then, it is neutralized with sodium bicarbonate solution, extracted with ethyl acetate, washed with water as well as common salt solution, dried on sodium sulfate and evaporated to the dry state in a vacuum. 0.2 g of crude 3,17-dihydroxy-11-{5-[methyl-(6,6,7,7,8,8,8-heptafluoro-octyl)-amino]-pentyl}-19-nor-17-pregna-1,3,5 (10)-trien-21,16-lactone is obtained, and after chromatography on silica gel with dichloromethane/ethyl acetate, 55 mg of pure 3,17-dihydroxy-11-{5-[methyl-(6,6,7,7,8,8,8-heptafluoro-octyl)-amino]-pentyl}-19-nor-17-pregna-1,3,5 (10)-triene-21,16-lactone is obtained. [a]D=+30.0° in chloroform.

Production of the Starting Compound: 6,6,7,7,8,8,8-Heptafluoro-octyl-methylamine a) 6,6,7,7,8,8,8-Heptafluoro-octylmethanesulfonate A solution of 37.2 g of 6,6,7,7,8,8,8-heptafluoro-octanol [Kuwamura, Tsunehiko; Ohshima, Masataka; Kameyama, Eiichi. *Nippon Kagaku Katshi* (1974), (3), 545–551] in 364 ml of methyl tert-butyl ether and 32.5 ml of triethylamine is slowly mixed with a solution of 17.4 ml of mesyl chloride in 100 ml of methyl tert-butyl ether, and it is stirred for one hour at 5° C. Then, it is neutralized with 182 ml of sodium bicarbonate solution, washed with water as well as common salt solution, dried on sodium sulfate and evaporated to the dry state in a vacuum. 44.7 g of 6,6,7,7,8,8,8-heptafluoro-octylmethanesulfonate is obtained as an oil.

b) 6,6,7,7,8,8,8-Heptafluoro-octyl-methylamine

In a solution of 44.7 g of 6,6,7,7,8,8,8-heptafluoro-octylmethanesulfonate in 134 ml of tetrahydrofuran, 41.5 g of methylamine is condensed at −78° C. and stirred for 24 hours at room temperature in a pressurized reactor. Then, it is evaporated to the dry state in a vacuum, washed with water as well as common salt solution, dried on sodium sulfate and evaporated to the dry state in a vacuum. 34.9 g of crude 6,6,7,7,8,8,8-heptafluoro-octyl-methylamine is obtained, and after distillation, 21 g of pure 6,6,7,7,8,8,8-heptafluoro-octyl-methylamine with a boiling point of 89–93° C. at 69 mbar is obtained.

The entire disclosures of all applications, patents and publications, cited herein and of corresponding Germany Patent Application No. 102 14 179.7, filed Mar. 27, 2002, and U.S. Provisional Application Ser. No. 60/374,517, filed Apr. 23, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 19-Nor-17α-pregna-1,3,5(10)-triene with a 21,16α-lactone ring of formula (II)

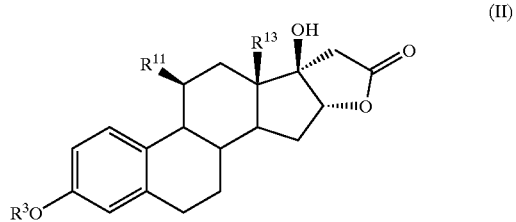

(II)

in which $R^3$ represents a hydrogen atom, a $C_{1-4}$-alkyl, $C_{2-6}$-acyl or tri($C_{1-4}$-alkyl)silyl group or $R^{18}SO_2$—, $R^{18}$ represents $R^{19}R^{20}N$—, $R^{19}$ and $R^{20}$ independently of one another, are a hydrogen atom, a $C_{1-5}$-alkyl radical, or $C(O)R^{21}$, $R^{21}$ represents a straight-chain or branched hydrocarbon radical with up to 6 carbon atoms, a $C_{3-7}$-cycloalkyl radical, an aryl radical, an aralkyl radical or an alkylaryl radical, $R^{11}$ represents a radical of formula —B-Z-$R^{22}$, B stands for a straight-chain or branched-chain alkylene with 4 to 9 carbon atoms, Z stands for —$NR^{23}$, $R^{23}$ stands for a $C_1$–$C_3$-alkyl group, $R^{22}$ stands for a hydrogen atom, a straight-chain or branched-chain alkyl, alkenyl or alkinyl group with 3 to 11 carbon atoms or for -D-$C_nF_{2n+1}$, D is a straight-chain or branched-chain alkylene, alkenylene or alkinylene group with 3 to 11 carbon atoms, n is an integer of 1 to 5, and $R^{13}$ stands for a methyl or ethyl group.

2. A 11β-Substituted 19-nor-17α-pregna-1,3,5(10)-triene with a 21,16α-lactone ring according to claim 1, in which $R^3$ is a hydrogen atom.

3. A 11β-Substituted 19-nor-17α-pregna-1,3,5(10)-triene with a 21,16α-lactone ring according to claim 1, in which $R^{11}$ is

—$(CH_2)_5N(CH_3)(CH_2)_3C_2F_5$,

—$(CH_2)_5N(CH_3)(CH_2)_6C_2F_5$,

—$(CH_2)_5N(CH_3)(CH_2)_7C_2F_5$,

—$(CH_2)_5N(CH_3)(CH_2)_8C_2F_5$,

—$(CH_2)_6N(CH_3)(CH_2)_6C_2F_5$,

—$(CH_2)_6N(CH_3)(CH_2)_7C_2F_5$,

—$(CH_2)_6N(CH_3)(CH_2)_8C_2F_5$,

—$(CH_2)_5N(CH_3)(CH_2)_2C_3F_7$,

—$(CH_2)_5N(CH_3)(CH_2)_6C_3F_7$,

—$(CH_2)_5N(CH_3)(CH_2)_2C_4F_9$,

—$(CH_2)_5N(CH_3)(CH_2)_6C_4F_9$,

—$(CH_2)_5N(CH_3)(CH_2)_2C_5F_{11}$,

—$(CH_2)_5N(CH_3)(CH_2)_6C_5F_{11}$,

—$(CH_2)_5N(CH_3)H$,

—$(CH_2)_5N(CH_3)(CH_2)_3H$,

—$(CH_2)_5N(CH_3)(CH_2)_6H$,

—$(CH_2)_5N(CH_3)(CH_2)_7H$,

—$(CH_2)_5N(CH_3)(CH_2)_9H$, or

—$(CH_2)_5N(CH_3)CH_2CH=CH—C_2F_5$.

4. A 11β-Substituted 19-nor-17α-pregna-1,3,5(10)-triene with a 21,16α-lactone ring according to claim 1, which is 3,17α-Dihydroxy-11β-{5-[methyl-(4,4,5,5,5-pentafluoro-pentyl)-amino]-pentyl}-19-nor-17α-pregna-1,3,5(10)-triene-21,16α-lactone, 3,17α-dihydroxy-11β-{5-[methyl-(7,7,8,8,8-pentafluoro-octyl)-amino]-pentyl}-19-nor-17α-pregna-1,3,5(10)-triene-21,16α-lactone, 3,17α-dihydroxy-11β-{5-[methyl-(8,8,9,9,9-pentafluoro-nonyl)-amino]-pentyl}-19-nor-17α-pregna-1,3,5(10)-triene-21,16α-lactone, 3,17α-dihydroxy-11β-{5-[methyl-(9,9,10,10,10-pentafluoro-decyl)-amino]-pentyl}-19-nor-17α-pregna-1,3,5(10)-triene-21,16α-lactone, 3,17α-dihydroxy-11β-{6-[methyl-(7,7,8,8,8-pentafluoro-octyl)-amino]-hexyl}-19-nor-17α-pregna-1,3,5(10)-triene-21,16α-lactone, 3,17α-dihydroxy-11β-{6-[methyl-(8,8,9,9,9-pentafluoro-nonyl)-amino]-hexyl}-19-nor-17α-pregna-1,3,5(10)-triene-21,16α-lactone, 3,17α-dihydroxy-11β-{6-[methyl-(9,9,10,10,10-pentafluoro-decyl)-amino]-hexyl}-19-nor-17α-pregna-1,3,5(10)-triene-21,16α-lactone, 3,17α-dihydroxy-11β-{5-[methyl-(3,3,4,4,5,5,5-heptafluoro-pentyl)-amino]-pentyl}-19-nor-17α-pregna-1,3,5(10)-triene-21,16α-lactone, 3,17α-dihydroxy-11β-{5-[methyl-(7,7,8,8,9,9,9-heptafluoro-nonyl)-amino]-pentyl}-19-nor-17α-pregna-1,3,5(10)-triene-21,16α-lactone, 3,17α-dihydroxy-11β-{5-[methyl-(3,3,4,4,5,5,6,6,6-nonafluoro-hexyl)-amino]-pentyl}-19-nor-17α-pregna-1,3,5(10)-triene-21,16α-lactone, 3,17α-dihydroxy-11β-{5-[methyl-(7,7,8,8,9,9,10,10,10-nonafluoro-decyl)-amino]-pentyl}-19-nor-17α-pregna-1,3,5(10)-triene-21,16α-lactone, 3,17α-dihydroxy-11β-{5-[methyl-(3,3,4,4,5,5,6,6,7,7,7-undecafluoro-heptyl)-amino]-pentyl}-19-nor-17α-pregna-1,3,5(10)-triene-21,16α-lactone, 3,17α-dihydroxy-11β-{5-[methyl-(7,7,8,8,9,9,10,10,11,11,11-undecafluoro-undecyl)-amino]-pentyl}-19-nor-17α-pregna-1,3,5(10)-triene-21,16α-lactone, 3,17α-dihydroxy-11β-{5-[methyl-amino]-pentyl}-19-nor-17α-pregna-1,3,5(10)-triene-21,16α-lactone, 3,17α-dihydroxy-11β-{5-[methyl-propyl-amino]-pentyl}-19-nor-17α-pregna-1,3,5(10)-triene-21,16α-lactone, 3,17α-dihydroxy-11β-{5-[methyl-hexyl-amino]-pentyl}-19-nor-17α-pregna-1,3,5(10)-triene-21,16α-lactone, 3,17α-dihydroxy-11β-{5-[methyl-heptyl-amino]-pentyl}-19-nor-17α-pregna-1,3,5(10)-triene-21,16α-lactone, 3,17α-dihydroxy-11β-{5-[methyl-nonyl-amino]-pentyl}-19-nor-17α-pregna-1,3,5(10)-triene-21,16α-lactone.

5. A pharmaceutical composition comprising a compound of formula II according to claim 1 and a pharmaceutically compatible vehicle.

6. A method for preparing a pharmaceutical composition according to claim 5, comprising bringing into a composition a compound of formula II and a pharmaceutically compatible vehicle.

7. A method for treating an estrogen-dependent disease, comprising administering to a patient in need thereof an effective amount of a pharmaceutical composition according to claim 5.

8. A method for treating breast cancer, endometrial carcinoma or prostate cancer, comprising administering to a patient in need thereof an effective amount of a pharmaceutical composition according to claim 5.

9. A pharmaceutical composition comprising a compound of formula II according to claim 2 and a pharmaceutically compatible vehicle.

10. A pharmaceutical composition comprising a compound of formula II according to claim 3 and a pharmaceutically compatible vehicle.

11. A pharmaceutical composition comprising a compound of formula II according to claim 4 and a pharmaceutically compatible vehicle.

12. A method for treating an estrogen-dependent disease, comprising administering to a patient in need thereof an effective amount of a pharmaceutical composition according to claim 9.

13. A method for treating an estrogen-dependent disease, comprising administering to a patient in need thereof an effective amount of a pharmaceutical composition according to claim 10.

14. A method for treating an estrogen-dependent disease, comprising administering to a patient in need thereof an effective amount of a pharmaceutical composition according to claim 11.

15. A method for treating breast cancer, endometrial carcinoma or prostate cancer, comprising administering to a patient in need thereof an effective amount of a pharmaceutical composition according to claim 9.

16. A method for treating breast cancer, endometrial carcinoma or prostate cancer, comprising administering to a patient in need thereof an effective amount of a pharmaceutical composition according to claim 10.

17. A method for treating breast cancer, endometrial carcinoma or prostate cancer, comprising administering to a patient in need thereof an effective amount of a pharmaceutical composition according to claim 11.

* * * * *